(12) United States Patent
Sumera et al.

(10) Patent No.: US 10,610,474 B1
(45) Date of Patent: Apr. 7, 2020

(54) ANTIBACTERIAL AND ANTIFUNGAL DENTAL HEALTH FORMULATION

(71) Applicant: Matthias W Rath, Aptos, CA (US)

(72) Inventors: Waldemar Sumera, Sanjose, CA (US); Matthias W Rath, Aptos, CA (US); Anna Goc, Sanjose, CA (US); Aleksandra Niedzwiecki, Aptos, CA (US)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 16/584,870

(22) Filed: Sep. 26, 2019

Related U.S. Application Data

(63) Continuation-in-part of application No. 16/226,698, filed on Dec. 20, 2018, now Pat. No. 10,463,590.

(51) Int. Cl.
| | | |
|---|---|---|
| *A61K 8/41* | (2006.01) |
| *A61Q 11/00* | (2006.01) |
| *A61K 8/9789* | (2017.01) |
| *A61K 8/36* | (2006.01) |
| *A61K 8/49* | (2006.01) |
| *A61K 8/92* | (2006.01) |

(52) U.S. Cl.
CPC ............ *A61K 8/411* (2013.01); *A61K 8/361* (2013.01); *A61K 8/4973* (2013.01); *A61K 8/922* (2013.01); *A61K 8/9789* (2017.08); *A61Q 11/00* (2013.01)

(58) Field of Classification Search
None
See application file for complete search history.

(56) References Cited

U.S. PATENT DOCUMENTS

| | | | | |
|---|---|---|---|---|
| 2011/0098495 A1* | 4/2011 | Huang | ...................... | C11C 1/08 554/224 |
| 2014/0056951 A1* | 2/2014 | Losick | ................... | A01N 33/04 424/400 |

FOREIGN PATENT DOCUMENTS

| | | | | |
|---|---|---|---|---|
| EP | 0256566 B1 * | 11/1991 | ............... | A61K 8/42 |
| WO | WO2000062751 A2 * | 10/2000 | ............... | A61K 7/26 |

* cited by examiner

*Primary Examiner* — Celeste A Roney
(74) *Attorney, Agent, or Firm* — Geeta Kadambi; Riddhi IP LLC

(57) ABSTRACT

A mixture, comprising at least three, two or four different chemical compounds, selected from the group eicosapentaenoic acid, usnic acid, norspermidine, clove oil and 10-undecynoic acid is used in dental health compositions. The mixture is used for dental hygiene for controlling *Streptococcus mutans* and *Candida albicans*.

9 Claims, 10 Drawing Sheets

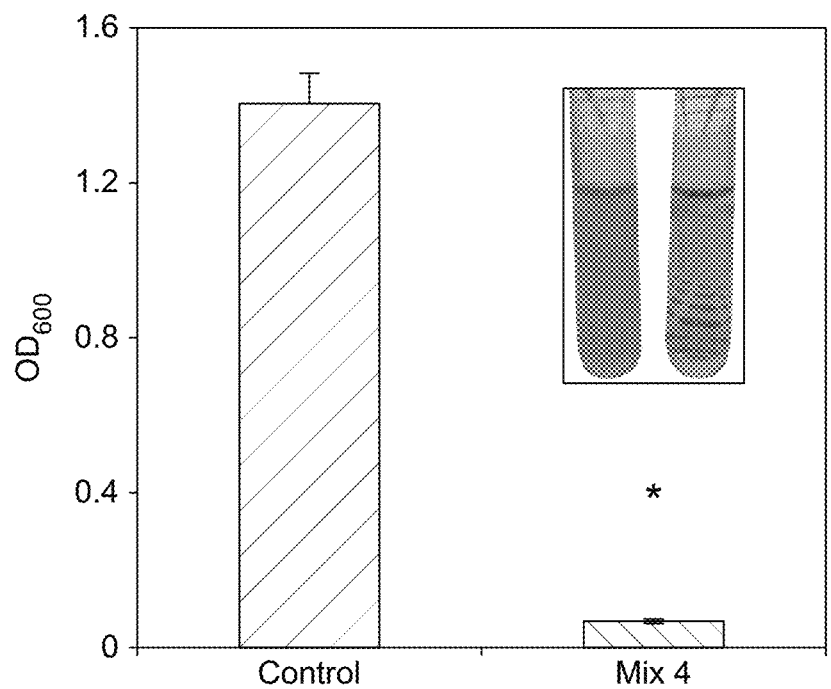
FIG. 2A  *p≤0.001
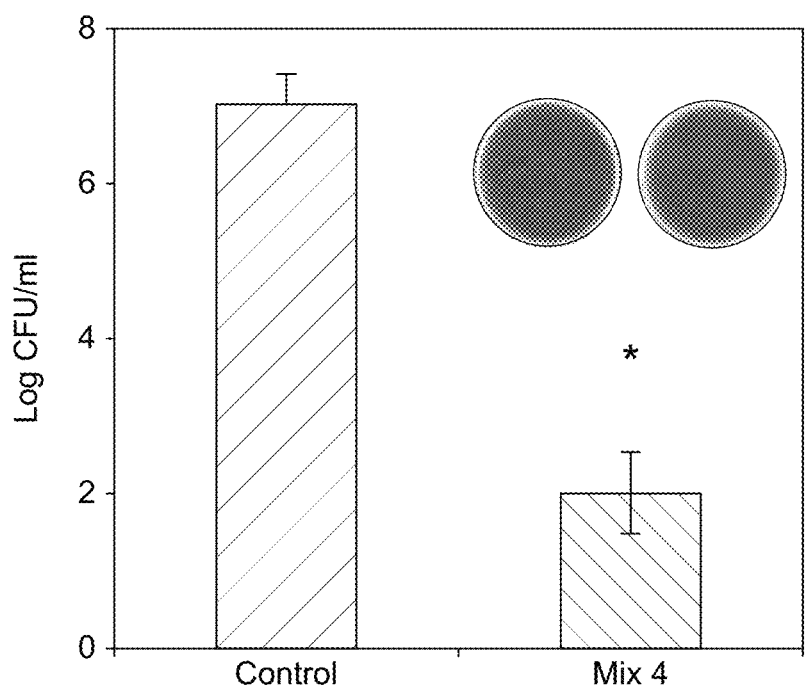
FIG. 2B  *p≤0.001

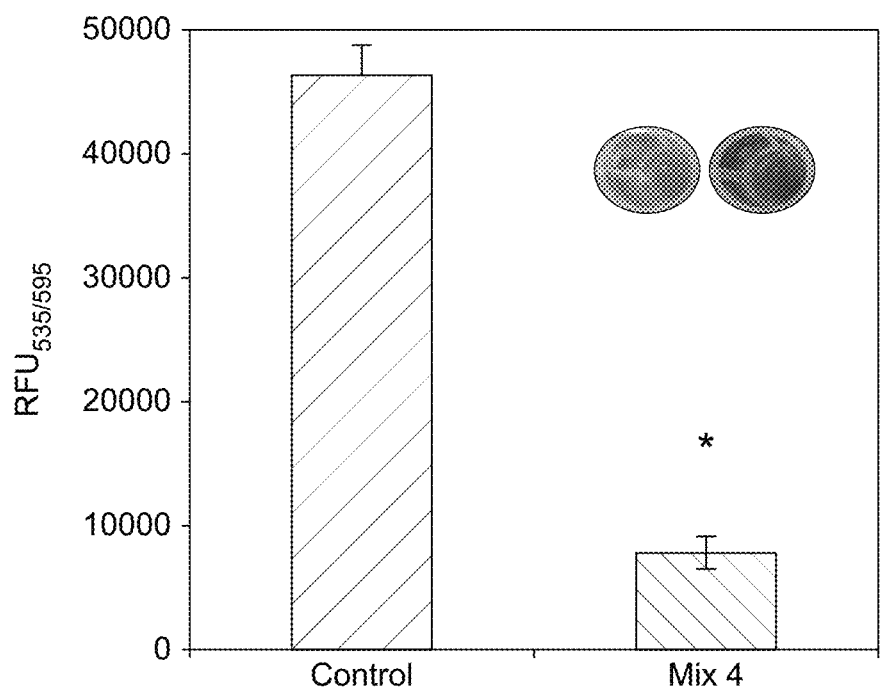
FIG. 3A  * p≤0.001
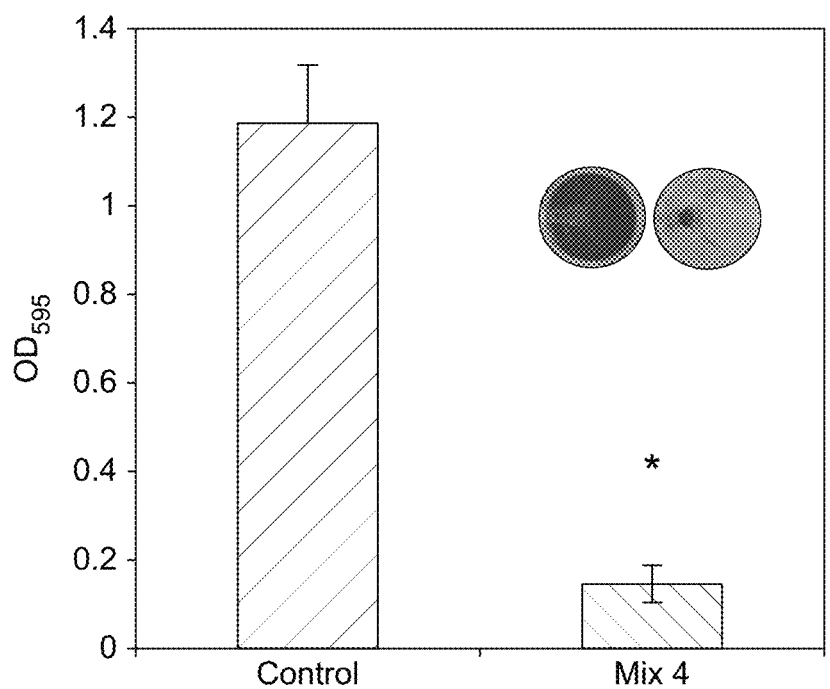
FIG. 3B  * p≤0.001

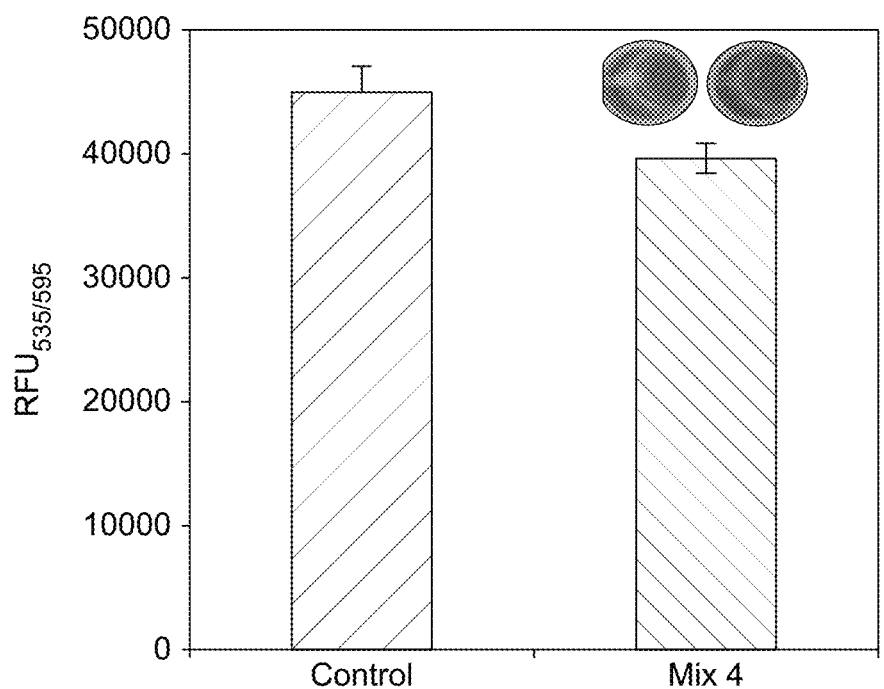
FIG. 4A  p≤0.054
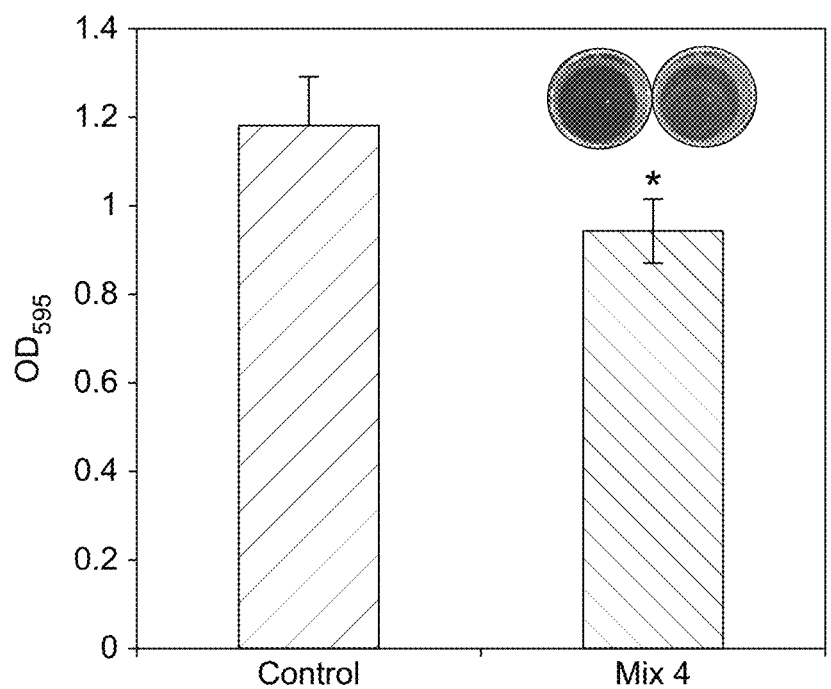
FIG. 4B  p≤0.055

ANTIBACTERIAL AND ANTIFUNGAL DENTAL HEALTH FORMULATION

CROSS REFERENCE TO RELATED APPLICATION

This application is a continuation in part application for pending U.S. application Ser. No. 16/226,698 filed on Dec. 20, 2018. The pending U.S. application Ser. No. 16/226,698 is hereby incorporated by reference in its entireties for all of its teachings.

FIELD OF INVENTION

This invention relates to an antibacterial dental formulation.

BACKGROUND

The tooth surface is covered with a biofilm—a slime layer consisting of millions of bacterial cells, salivary polymers, and food debris. This biofilm can easily reach a thickness of hundreds of cells on the surfaces of the teeth. The formed biofilm, also called plaque, provides an excellent adhesion site for the colonization and growth of many bacterial species. Bacteria live in these communities to protect themselves from threats like other germs, antibiotics or antimicrobials. The plaque that forms on teeth is a type of dental biofilm, and because it can lead to oral health problems like gum disease or cavities, it needs to be removed promptly. Three effective mechanical methods for biofilm removal are brushing, flossing and furthermore professional cleanings which remove biofilm, plaque and tartar from above and below the gumline with special instruments.

*Streptococcus mutans* comprises a group of seven closely related species collectively referred to as the *mutans* streptococci. The primary habitats for *S. mutans* are mouth, pharynx, and intestine. *S. mutans* and *S. sorbinus* can adhere to the tooth enamel and to other plaque bacteria and play a central role in the etiology of dental caries. *Mutans* streptococci are responsible for developing tooth cavities.

Currently, oral biofilm control is primarily accomplished through the use of dentifrice containing compounds such as detergents, abrasives and antimicrobials, which achieve their effects in conjunction with mechanical tooth brushing. If biofilm accumulation and growth can be reduced and its re-aggregation discouraged, this will result in improved gingival health. Conversely, ineffective plaque control is directly implicated in gingival inflammation and eventually in destructive chronic periodontitis. Despite its essential role in the prevention of gingivitis and periodontitis, and often considerable efforts at oral hygiene by patients, effective and stable plaque control remains elusive to many individuals. Accordingly, a multitude of novel anti-plaque formulations are under investigation for their ability to remove oral biofilm and to prevent its re-accumulation.

The pending application has more ingredients and more effective formulation needs to be discovered.

SUMMARY

The instant description provides an anti-plaque composition, which has bactericidal and bacteriostatic effects against *S. mutans* and yeast *Candida albicans*, which prevents the formation of and leads to the removal of dental biofilm and is effective for the prevention and treatment of dental caries.

A mixture, consists of at least four different chemical compound or two different chemical compound or three different chemical compound from a *B. Serrata* Extract, eicosapentaenoic acid, usnic acid, 10-undecynoic acid, clove oil and norspermidine. The mixture that consists of at least four different chemical compounds wherein a concentration of the Norspermidine the Usnic acid, the eicosapentaenoic acid and the *B. serrata* extract, wherein the Norspermidine is 0.1% of total weight, the Usnic acid is 50 µg/ml, the eicosapentaenoic acid is 50 µg/ml and the *B. serrata* extract is 250 µg/ml.

In another embodiment, two different chemical compounds make the dental formulation as a treatment compound, wherein the mixture consists of the Norspermidine (0.1%) and Usnic acid (50 µg/ml).

In one embodiment the mixture is an anti-plaque dental composition comprising in a liquid or paste-like or solid carrier material. The object is furthermore achieved by an anti-caries dental composition comprising this mixture in a liquid or paste-like or solid carrier material.

In another embodiment, a dental composition with bactericidal and bacteriostatic effectiveness against *S. mutans* and *Candida albicans*, comprising this mixture. The object is furthermore achieved by a composition comprising this mixture for the treatment or prevention of dental caries or dental biofilm.

The object is furthermore achieved by a method for forming a mixture or composition as described above by admixing the ingredients of the mixture or composition.

According to the present invention it has been found that a specific composition of natural compounds has bactericidal and bacteriostatic effects against *S. mutans* and *Candida albicans*, thereby allowing the prevention and treatment of dental caries and dental biofilm.

The specific combination of the ingredients of the composition or mixture leads to a bactericidal and bacteriostatic effect, which is far superior to the effect of each of the ingredients alone.

BRIEF DESCRIPTION OF DRAWINGS

Example embodiments are illustrated by way of example and not limitation in the figures of the accompanying drawings, in which like references indicate similar elements and in which:

FIG. 2A. 100% bacteriostatic effect was achieved with the test mix 4 in one concentration after 24 h incubation against planktonic form of oral *Streptococcus mutans*.

FIG. 2B. 100% bactericidal effect was achieved with the test mix 4 in another concentration after 24 h incubation against planktonic form of oral *Streptococcus mutans*.

FIG. 3A. 100% biofilm biocidal effect was achieved with the test mix 4 in one concentration after 24 h incubation against oral *Streptococcus mutans*.

FIG. 3B. 100% biofilm growth inhibition was achieved with the test mix 4 after 24 h incubation against oral *Streptococcus mutans*.

FIG. 4A. Modest bactericidal effect was achieved with the test mix 4 in one concentration after 24 h incubation against oral *Streptococcus mutans*.

FIG. 4B. Modest mature biofilm eradication effect was achieved with the test mix 4 in another concentration after 24 h incubation against oral *Streptococcus mutans*.

Figure 1A:
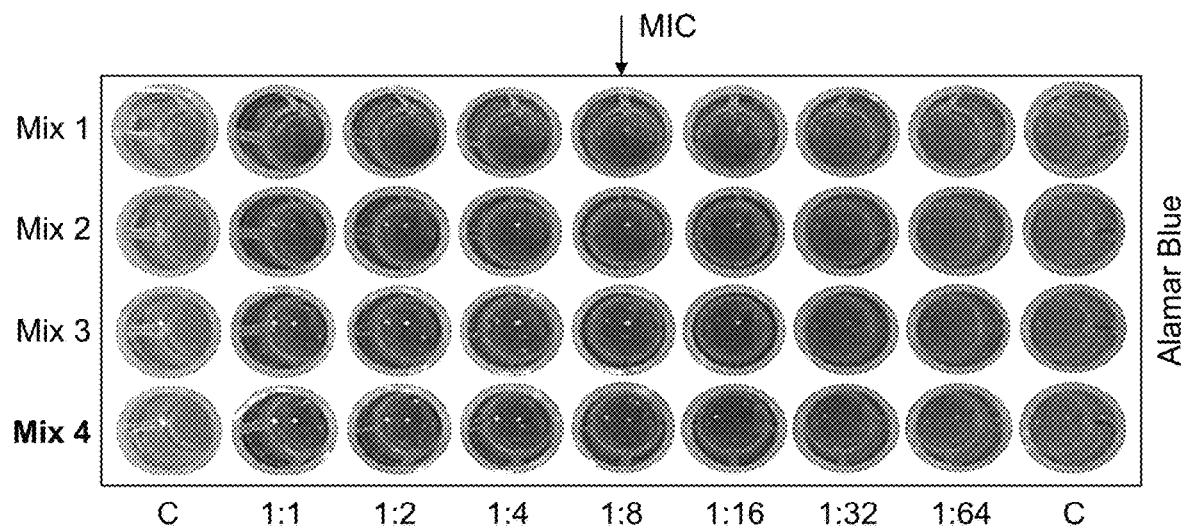
FIG. 1A. Mix 1-4 showed the highest preventive potency against biofilm formation and growth of *Streptococcus mutans*.

Others features of the present embodiments will be apparent from the accompanying drawings and from the detailed description that follows.

DETAILED DESCRIPTION

The mixture according to the present invention comprises at least four different chemical compounds, preferably at least five different chemical compounds, more preferably at least six different chemical compounds, and most preferably all seven of the chemical compounds listed above. In a preferred embodiment, the mixture comprises additionally at least one essential oil as indicated above.

The ingredients per se are known natural compounds. The term "natural compounds" defines compounds that occur in nature or natural products and can be isolated from these natural products. Thus, the term "natural compounds" can be contrasted to "synthetic compounds" which are prepared in a chemical synthesis reaction, whereas the natural compounds are derived from, extracted from or obtained from natural sources. Preferably, the natural compounds discussed below are obtained from natural sources by extraction, distillation, crystallization in a known manner Materials and Methods Test Compounds.

The following compounds, with the purity between 90%-98% according to the manufacturer, were obtained from Sigma (St. Louis, Mo.): usnic acid, norspermidine, *Boswellia serrata* extract. Eicosapentaenoic acid (EPA) with the purity between 97%-99% according to the manufacturer was purchased from Cayman Chemical (Ann Arbor, Mich.).

Preparation of test compounds for susceptibility testing. A stock solution of (10-50 mg/ml) of all compounds (depending on solubility of each substance) was prepared by suspending each of the test compounds in absolute ethanol and sterilized by 0.22 µm syringe filtration. All stock solutions were stored in aluminum foil-wrapped tubes at −20° C. Since a high percentage of ethanol could be bactericidal, the amount of ethanol added to the growth medium was kept as low as possible. A preliminary experiment determined that ethanol content should not exceed the maximum percentage of DMSO, established as 0.5% (v/v). In our experiments, the final concentration of DMSO present in the growth medium was kept below 0.4% (v/v). The appropriate amount of each stock solution was added to either sterile two-position-cap test tubes containing 1 ml of BHI (Brain Heart Infusion) broth or to 96-well plates containing 200 µl of BHI broth to yield final concentrations of 10-50 µg/ml. As a negative control, DMSO at 0.1-0.4% (v/v) was applied.

Test microorganism. *Streptococcus mutans* AU159 strain, obtained from the American Type Culture Collection (Manassas, Va.), were tested in their two morphological forms: cocci planktonic form and biofilm. The stocks of both species were cultured in commonly used conditions, i.e., BHI broth (Remel, San Diego, Calif.) without antibiotics at 37° C. with 5% $CO_2$, in sterile two-position cap 5 ml polypropylene test tubes.

Evaluation of bacteriostatic effect of test mix on *Streptococcus mutans*. Growth inhibition of *Streptococcus mutans* was tested using standard macro-dilution method according to guidance of American Society for Microbiology to establish MIC (Minimal Inhibitory Concentration) value. Briefly, sterile 3 ml test two-position capped tubes containing 1 ml BHI broth, supplemented with the test mix was inoculated with $1 \times 10^7$ CFU/ml of the homogenous bacterial suspension. The tubes were then incubated at 37° C. with 5% $CO_2$ and growth inhibition as a decrease in the optical density (OD600) was measured after 24 h. The entire experiment was repeated three times for each strain. Control cultures were treated with DMSO (i.e., 0.1-0.4 v/v) alone.

Evaluation of bactericidal effect of test mix on *Streptococcus mutans* Killing efficacy against *Streptococcus mutans* was determined from macro-broth dilution minimum inhibitory concentration by sub-culturing it to BHI agar plates that do not contain the test mix, which is a standard procedure, performed according to guidance of American Society for Microbiology, to establish MBC (Minimal Bactericidal Concentration) value. Briefly, samples with visible growth inhibition after 24 h incubation with the test mix were plated on sterile BHI agar plates that do not contain the test mix. The plates were then incubated at 37° C. with 5% $CO_2$ and bacterial re-growth was assessed after 24 h. The entire experiment was repeated three times for each strain. Control cultures were treated with DMSO (i.e., 0.1-0.4 v/v).

Evaluation of preventive effect of test mix on *Streptococcus mutans* biofilm formation. Preventive effect of the test mix against biofilm of *Streptococcus mutans* was evaluated by the commonly used crystal violet (CV) staining method, according to guidance of American Society for Microbiology to establish MBIC (Minimal Biofilm Inhibitory Concentration) value. Briefly, 1×107 CFU/ml from homogeneous bacterial culture in BHI broth containing 1% sucrose, as a standard approach, was inoculated into saliva-coated 96-well plates and supplemented with the test mix. Control wells were treated with DMSO (i.e., 0.1-0.4 v/v) alone. All plates were then incubated at 37° C. with 5% CO2 for 24 h. Next, all wells were fixed with 200 µl of cold methanol-formalin (1:1) for 30 min and stained with 200 µl of crystal violet (0.1%) for 10 min. The biofilms were carefully washed three times with 1×PBS (phosphate-buffered saline), and 200 µl of methanol was added to each well to extract a dye which was measured at 595 nm using a spectrophotometer (Molecular Device, Spectra Max 340). In addition, supporting alamarBlue staining assay (where resazurin, a non-fluorescent indicator dye, is converted to bright red-fluorescent resorufin via the reduction reactions of metabolically active cells and the amount of fluorescence produced is proportional to the number of living cells) was performed for evaluating cellular health, according to guidance of American Society for Microbiology and manufacturer's protocol to establish MBBC (Minimal Biofilm Biocidal Concentration) value. The whole experiment was repeated three times.

Evaluation of eradication effect of test mix on *Streptococcus mutans* mature biofilm. Qualitative and quantitative efficacy of the test mix against biofilm of *Streptococcus mutans* was evaluated by the commonly used crystal violet (CV) staining method supported by alamarBlue staining assay (where resazurin, a non-fluorescent indicator dye, is converted to bright red-fluorescent resorufin via the reduction reactions of metabolically active cells and the amount of fluorescence produced is proportional to the number of living cells) for evaluating cellular health, according to guidance of American Society for Microbiology and manufacturer's protocol to establish MBEC (Minimal Biofilm Eradication Concentration) and MBBC (Minimal Biofilm Biocidal Concentration) values. Briefly, 1×107 CFU/ml from homogeneous bacterial culture in BHI broth containing 1% sucrose, as a standard approach, was inoculated into saliva-coated 96-well plates and supplemented with the test mix. Control wells were treated with DMSO (i.e., 0.1-0.4 v/v) alone. All plates were then incubated at 37° C. with 5% CO2 up to 24 h. Next, all wells were supplemented with 10 µl of ready-to-use alamarBlue day and read with spectrophotometer using 535EX nm/595EM nm filter settings followed by fixation with 200 µl of cold methanol-formalin (1:1) for 30 min. and staining with 200 µl of crystal violet (0.1%) for 10 min After the biofilms were carefully washed three times with 1×PBS (phosphate-buffered saline), 200 µl of methanol was added to each well to extract a dye which was measured at 595 nm using a spectrophotometer (Molecular Device, Spectra Max 340). The whole experiment was repeated three times.

Statistical analysis. All the data are presented as means±SD (n=3). The Student's two-tailed t test was used to determine statistically significant differences set at 0.05 levels. Statistical analysis was performed using GraphPad software.

Summary of Results: FIG. 1A. Mix4 showed the highest preventive potency against biofilm formation and growth of *Streptococcus mutans*. 100% biocidal effect was achieved with the test mix 4 (usnic acid 6.25 norspermidine 0.0125%, EPA 6.25 µg/ml, *B. serrata* extract 31.25 µg/ml) after 24 h incubation.

Figure 1B:
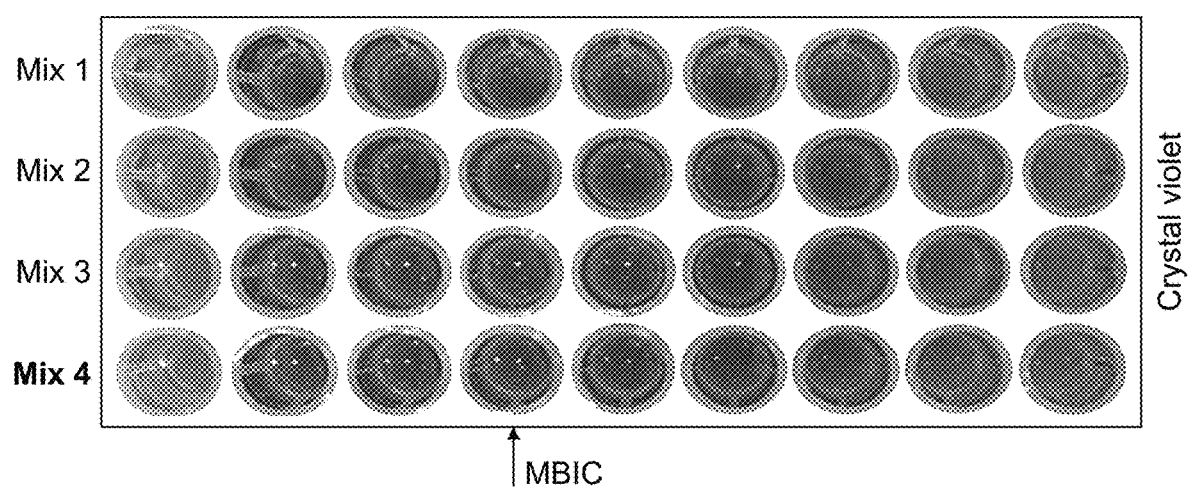
FIG. 1B. Mix 1-4 showed the highest preventive potency against biofilm formation and growth of *Streptococcus mutans* at different concentrations.

FIG. 1B. Mix4 showed the highest preventive potency against biofilm formation and growth of *Streptococcus mutans*. 100% growth inhibitory effect was achieved with the test mix 4 (usnic acid 12.5 norspermidine 0.025%, EPA 12.5 µg/ml, *B. serrata* extract 62.5 µg/ml) after 24 h incubation.

FIG. 2A. 100% bacteriostatic effect was achieved with the test mix 4 (usnic acid 6.25 norspermidine 0.0125%, EPA 6.25 µg/ml, *B. serrata* extract 31.25 µg/ml) after 24 h incubation against planktonic form of oral *Streptococcus mutans*.

FIG. 2B. 100% bactericidal effect was achieved with the test mix 4 (usnic acid 6.25 norspermidine 0.0125%, EPA 6.25 µg/ml, *B. serrata* extract 31.25 µg/ml) after 24 h incubation against planktonic form of oral *Streptococcus mutans*.

FIG. 3A. 100% biofilm biocidal effect was achieved with the test mix 4 (usnic acid 12.5 norspermidine 0.025%, EPA 12.5 µg/ml, *B. serrata* extract 62.5 µg/ml) after 24 h incubation against oral *Streptococcus mutans*.

FIG. 3B. 100% biofilm growth inhibition was achieved with the test mix 4 (usnic acid 12.5 norspermidine 0.025%, EPA 12.5 µg/ml, *B. serrata* extract 62.5 µg/ml) after 24 h incubation against oral *Streptococcus mutans*.

FIG. 4A. Modest bactericidal effect was achieved with the test mix 4 (usnic acid 50 norspermidine 0.1% EPA 50 µg/ml, *B. serrata* extract 250 µg/ml) after 24 h incubation against oral *Streptococcus mutans*.

FIG. 4B. Modest mature biofilm eradication effect was achieved with the test mix 4 (usnic acid 50 norspermidine 0.1%, EPA 50 µg/ml, *B. serrata* extract 250 µg/ml) after 24 h incubation against oral *Streptococcus mutans*.

Figure 5A:
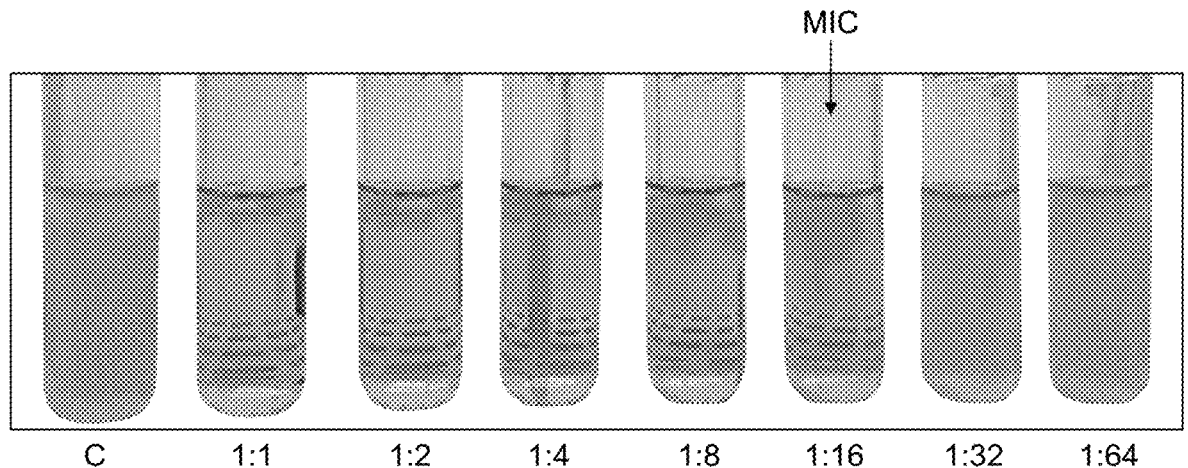
FIG. 5A. Mix 1 showed the highest bacteriostatic potency against planktonic form of *Streptococcus mutans*. 100% bacteristatic effect was achieved with the test mix 1 after 24 h incubation.
Figure 5B:
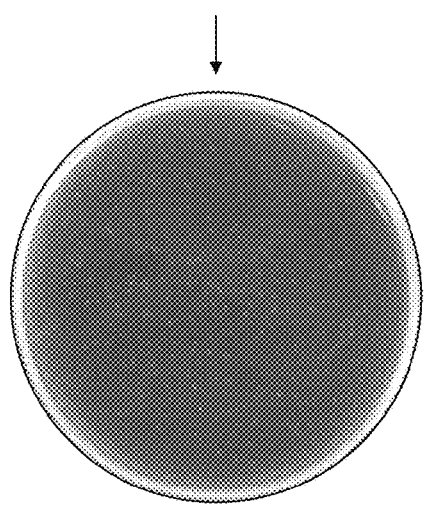
FIG. 5B. Mix 1 showed the highest bactericidal potency against planktonic form of *S. mutans*.
Figure 5C:
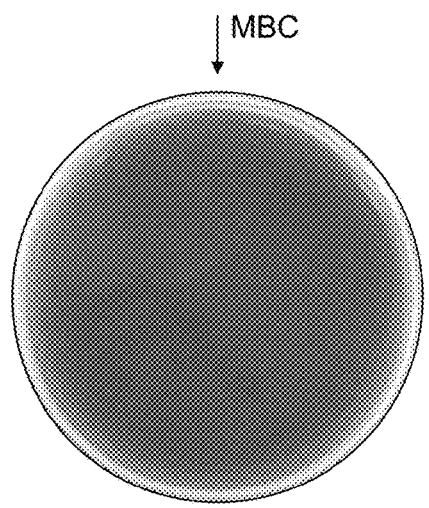
FIG. 5C is a control.

FIG. 5A. Mix1 showed the highest bacteriostatic potency against planktonic form of *Streptococcus mutans*. 100% bacteristatic effect was achieved with the test mix 1 (usnic acid 3.125 µg/ml, norspermidine 0.00625%) after 24 h incubation. FIG. 5B. Mix1 showed the highest bactericidal potency against planktonic form of *S. mutans*. 100% bactericidal effect was achieved with the test mix 1 (usnic acid 3.125 µg/ml, norspermidine 62.5 µg/ml) after 24 h incubation.

Test compounds. The following compounds, with the purity between 90%-98% according to the manufacturer, were obtained from Sigma (St. Louis, Mo.): 10-UDYA, clove oil. Eicosapentaenoic acid (EPA) with the purity between 97%-99% according to the manufacturer was purchased from Cayman Chemical (Ann Arbor, Mich.). Bacterial strain (*Streptococcus mutans*) and yeast strain (*Candida albicans*) were from ATCC (Manassas, Va.)

Preparation of test compounds for susceptibility testing. A stock solution of (10-200 mg/ml) of all compounds (depending on solubility of each substance) was prepared by suspending each of the test compounds in DMSO and sterilized by 0.22 µm syringe filtration. All stock solutions were stored in aluminum foil-wrapped tubes at −20° C. The appropriate amount of each stock solution was added to either sterile two-position-cap test tubes containing 1 ml of BHI broth (Brain Heart Infusion for *S. mutans*) or SD broth (Sabouraud Dextrose for *C. albicans*) or to 96-well plates containing 200 µl of BHI broth or SD broth to yield desired final concentrations. As a negative control, DMSO below 3% was applied.

Test microorganisms. Oral bacterium *Streptococcus mutans* AU159 strain and yeast *Candida albicans* 10231 strain, obtained from the American Type Culture Collection (Manassas, Va.), were tested in their two morphological forms: planktonic and biofilm. The stocks of both species were cultured in commonly used conditions, i.e., BHI broth (Remel, San Diego, Calif.) and SD broth (Remel, San Diego, Calif.) without antibiotics at 37° C. with 5% CO2, in sterile two-position cap 5 ml polypropylene test tubes.

Evaluation of bacteriostatic effect of test mix. Growth inhibition of Streptococcus mutans and Candida albicans was tested using standard macro-dilution method according to guidance of American Society for Microbiology to establish MIC (Minimal Inhibitory Concentration) value. Briefly, sterile 3 ml test two-position capped tubes containing 1 ml BHI or SD broth, supplemented with the test mix was inoculated with 1×107 CFU/ml of the bacterial or 1×107 cells/ml yeast suspension. The tubes were then incubated at 37° C. with 5% CO2 and growth inhibition as a decrease in the optical density (OD600) was measured after 24 h. The entire experiment was repeated three times for each strain. Control cultures were treated with DMSO (below 3%) alone.

Evaluation of bactericidal effect of test mix. Killing efficacy against Streptococcus mutans and Candida albicans was determined from macro-broth dilution minimum inhibitory concentration by sub-culturing it to BHI or SD agar plates that do not contain the test mix, which is a standard procedure, performed according to guidance of American Society for Microbiology, to establish MBC (Minimal Biocidal Concentration) value. Briefly, samples with visible growth inhibition after 24 h incubation with the test mix were plated on sterile BHI or SD agar plates that do not contain the test mix. The plates were then incubated at 37° C. with 5% CO2 and re-growth was assessed after 24 h. The entire experiment was repeated three times for each strain. Control cultures were treated with DMSO (below 3%) alone.

Evaluation of preventive effect of test mix on biofilm formation. Preventive effect of the test mix against biofilm of Streptococcus mutans and Candida albicans was evaluated by the commonly used crystal violet (CV) staining method, according to guidance of American Society for Microbiology to establish MBFC (Minimal Biofilm Formation Concentration) value. Briefly, 1×107 CFU/ml from bacterial culture in BHI broth containing 1% sucrose or 1×107 cells/ml from yeast culture in RPMI-1640 medium, as a standard approach, was inoculated into saliva-coated 96-well plates and supplemented with the test mix. Control wells were treated with DMSO (below 3%) alone. All plates were then incubated at 37° C. with 5% CO2 for 24 h. Next, all wells were fixed with 0.2 ml of cold methanol-formalin (1:1) for 30 min and stained with 0.1 ml of crystal violet (0.1%) for 10 min. The biofilms were carefully washed three times with 1×PBS (phosphate-buffered saline), and 0.2 ml of methanol was added to each well to extract a dye which was measured at 595 nm using a spectrophotometer (Molecular Device, Spectra Max 340). The whole experiment was repeated three times for each strain and each compound concentration.

Evaluation of eradication effect of test mix on mature biofilm. Qualitative and quantitative efficacy of the test mix against biofilm of Streptococcus mutans and Candida albicans was evaluated by the commonly used crystal violet (CV) staining method supported by alamarBlue staining assay (where resazurin, a non-fluorescent indicator dye, is converted to bright red-fluorescent resorufin via the reduction reactions of metabolically active cells and the amount of fluorescence produced is proportional to the number of living cells) for evaluating cellular health, according to guidance of American Society for Microbiology and manufacturer's protocol to establish MBEC (Minimal Biofilm Eradication Concentration) and MBBC (Minimal Biofilm Biocidal Concentration) values. Briefly, 1×107 CFU/ml from bacterial culture in BHI broth containing 1% sucrose or 1×107 cells/ml from yeast culture in RPMI-1640 medium, as a standard approach, was inoculated into saliva-coated 96-well plates and supplemented with the test mix. Control wells were treated with DMSO (below 3%) alone. All plates were then incubated at 37° C. with 5% CO2 up to 24 h. Next, all wells were supplemented with 10 µl of ready-to-use alamarBlue day and read with spectrophotometer using 535EX nm/595EM nm filter settings followed by fixation with 0.2 ml of cold methanol-formalin (1:1) for 30 min and staining with 0.1 ml of crystal violet (0.1%) for 10 min After the biofilms were carefully washed three times with 1×PBS (phosphate-buffered saline), 0.2 ml of methanol was added to each well to extract a dye which was measured at 595 nm using a spectrophotometer (Molecular Device, Spectra Max 340). The whole experiment was repeated three times for each strain and each compound concentration.

Statistical analysis. All the data are presented as means±SD (n=3). The Student's two-tailed t test was used to determine statistically significant differences set at 0.05 levels. Statistical analysis was performed using GraphPad software.

Figure 6A:
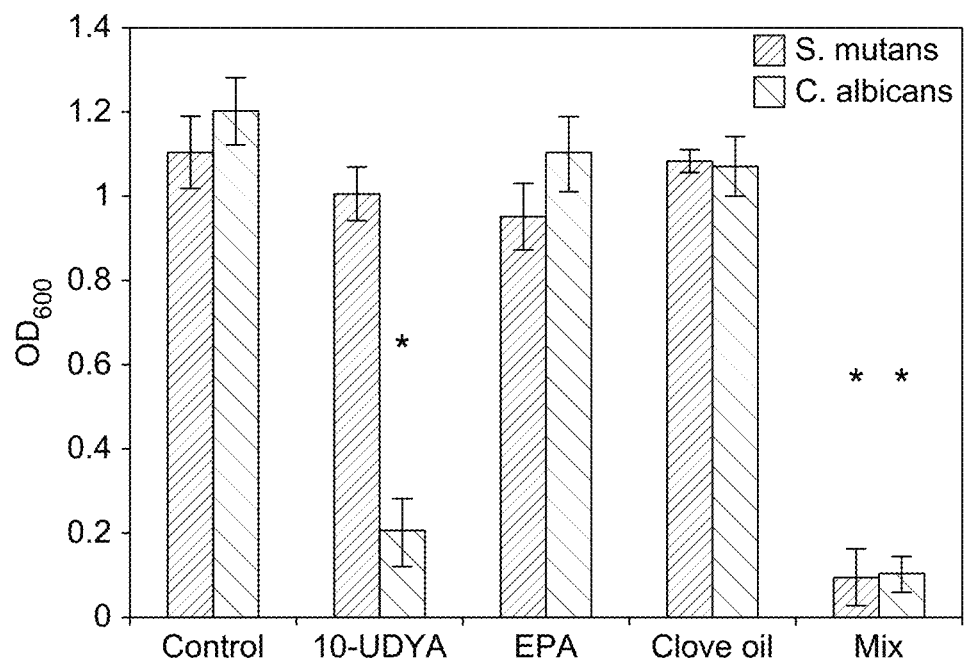
FIG. 6A. 100% inhibitory effect on planktonic form of *Streptococcus mutans* and *Candida albicans* was achieved with the test mix at 1525 µg/ml after 24 h incubation with the test mix.

Summary of Results: FIG. 6A. 100% inhibitory effect on planktonic form of Streptococcus mutans and Candida albicans was achieved with the test mix at 1525 µg/ml (10-UDYA 1000 µg/ml, EPA 25 µg/ml, clove oil 500 µg/ml) after 24 h incubation with the test mix.

Figure 6B:
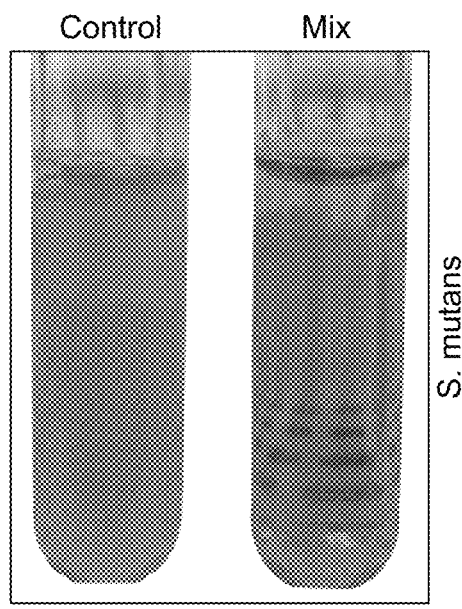
FIG. 6B. Representative images of *Streptococcus mutans* and FIG. 6C *Candida albicans* after 24 h incubation period with the test mix at 1525 µg/ml concentration.
Figure 6C:
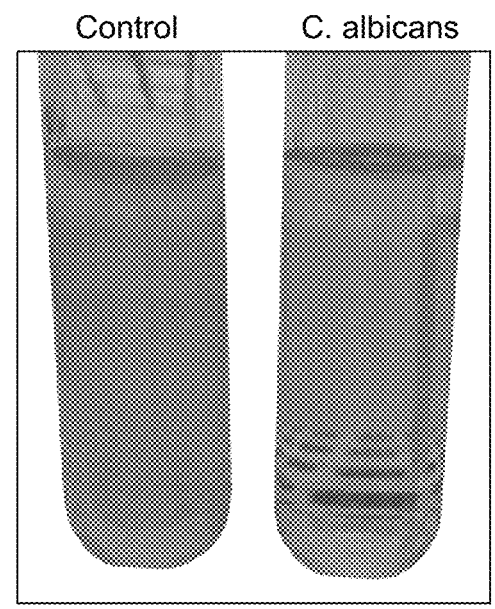

FIG. 6B. Representative images of Streptococcus mutans and FIG. 6C Candida albicans after 24 h incubation period with the test mix at 1525 µg/ml (10-UDYA 1000 µg/ml, EPA 25 µg/ml, clove oil 500 µg/ml) concentration.

Figure 7A:
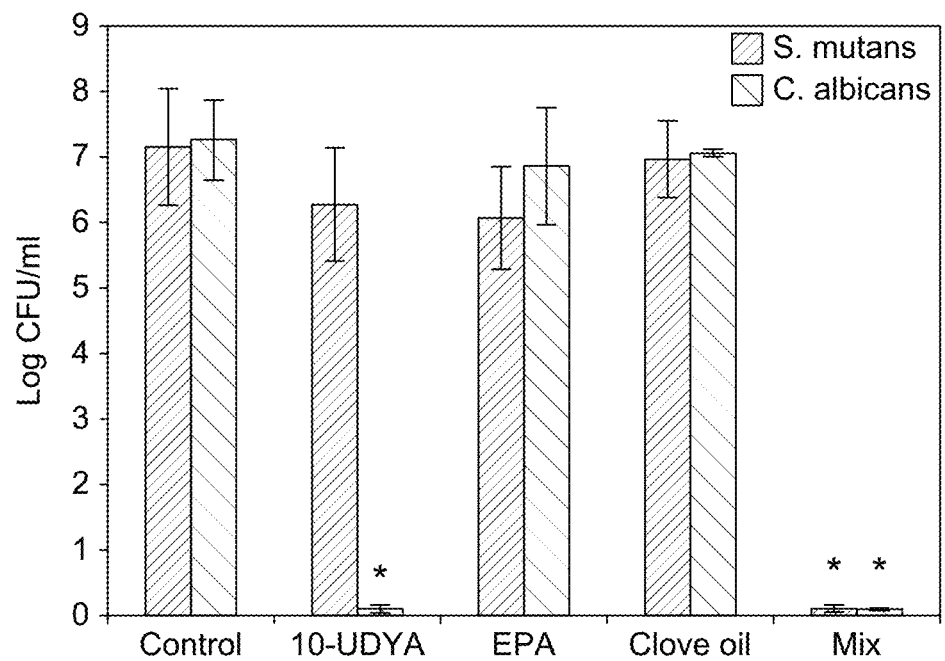
FIG. 7A. 100% biocidal effect on planktonic form of *Streptococcus mutans* and *Candida albicans* was achieved with the test mix at 3025-1525 µg/ml after 24 h incubation with the test mix.

FIG. 7 A. 100% biocidal effect on planktonic form of Streptococcus mutans and Candida albicans was achieved with the test mix at 3025-1525 µg/ml (10-UDYA 2500 µg/ml, EPA 25 µg/ml, clove oil 500 µg/ml for S. mutans and 10-UDYA 1000 µg/ml, EPA 25 µg/ml, clove oil 500 µg/ml for C. albicans) after 24 h incubation with the test mix.

Figures 7B, 7C:
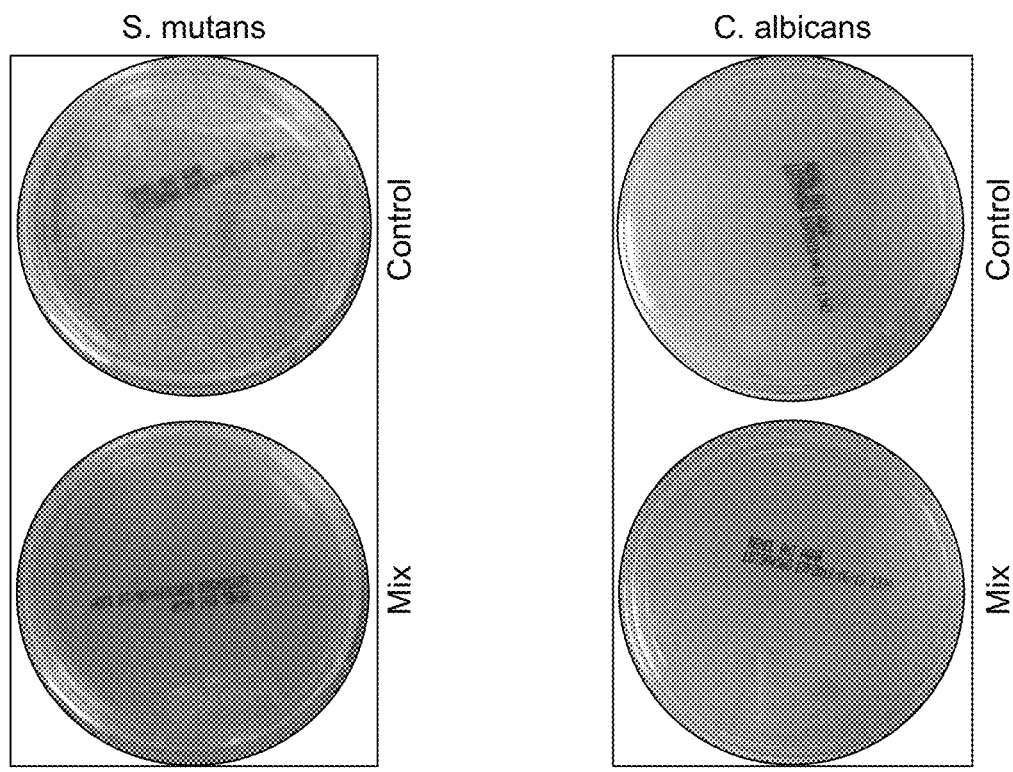
FIG. 7B. Representative images of *Streptococcus mutans* and FIG. 7C *Candida albicans* after 24 h incubation period with the test mix at 3025-1525 µg/ml concentration.

FIG. 7B. Representative images of Streptococcus mutans and FIG. 7C Candida albicans after 24 h incubation period with the test mix at 3025-1525 µg/ml (10-UDYA 2500 µg/ml, EPA 25 µg/ml, clove oil 500 µg/ml for S. mutans and 10-UDYA 1000 µg/ml, EPA 25 µg/ml, clove oil 500 µg/ml for C. albicans) concentration.

Figure 8A:
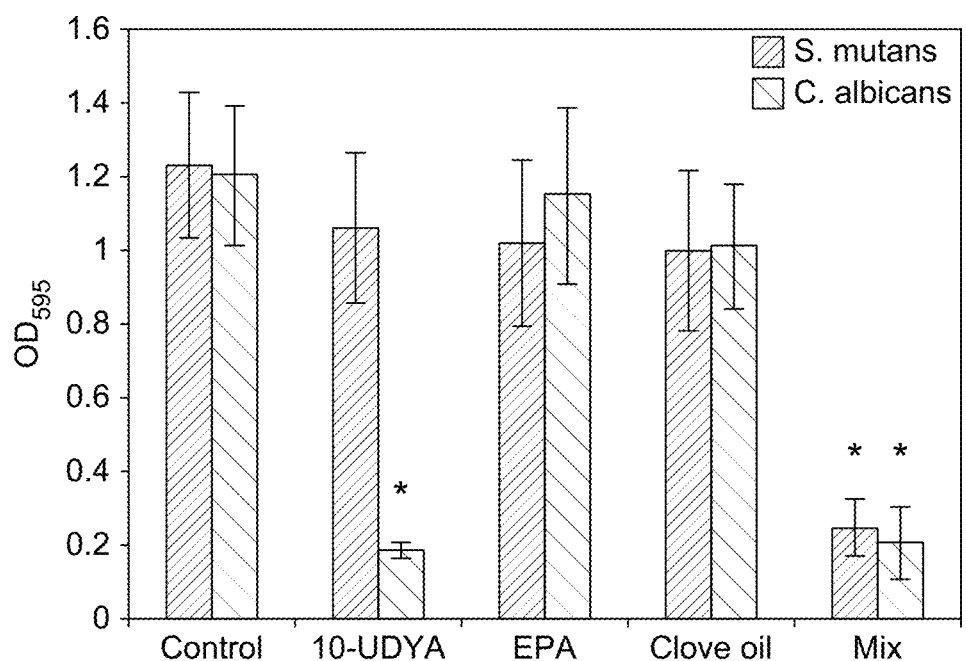
FIG. 8A. 100% preventive effect on biofilm formation of *Streptococcus mutans* and *Candida albicans* was achieved with the test mix at 1525 µg/ml after 24 h incubation with the test mix.

FIG. 8A. 100% preventive effect on biofilm formation of Streptococcus mutans and Candida albicans was achieved with the test mix at 1525 µg/ml (10-UDYA 1000 µg/ml, EPA 25 µg/ml, clove oil 500 µg/ml) after 24 h incubation with the test mix.

Figure 8B:
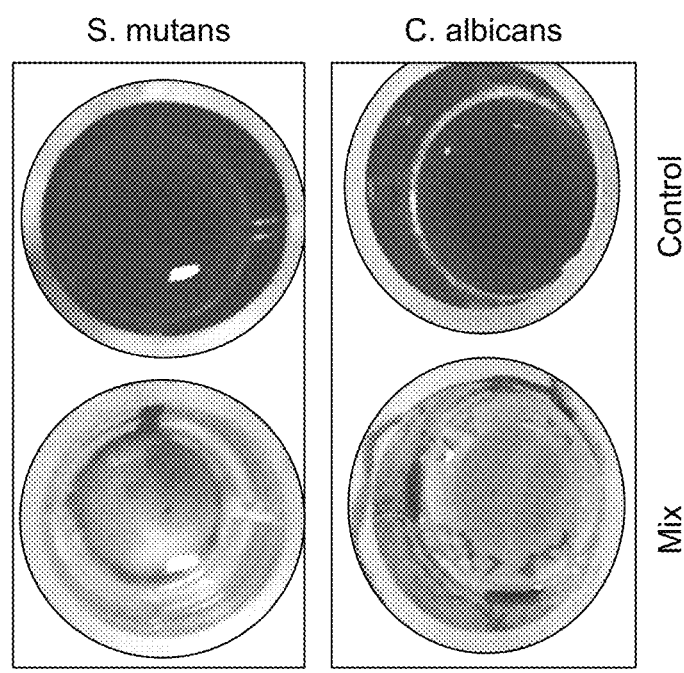
FIG. 8B. Representative images of *Streptococcus mutans* and *Candida albicans* after 24 h incubation period with the test mix at 1525 µg/ml concentration.

FIG. 8B. Representative images of Streptococcus mutans and Candida albicans after 24 h incubation period with the test mix at 1525 µg/ml (10-UDYA 1000 µg/ml, EPA 25 µg/ml, clove oil 500 µg/ml) concentration.

Figure 9A:
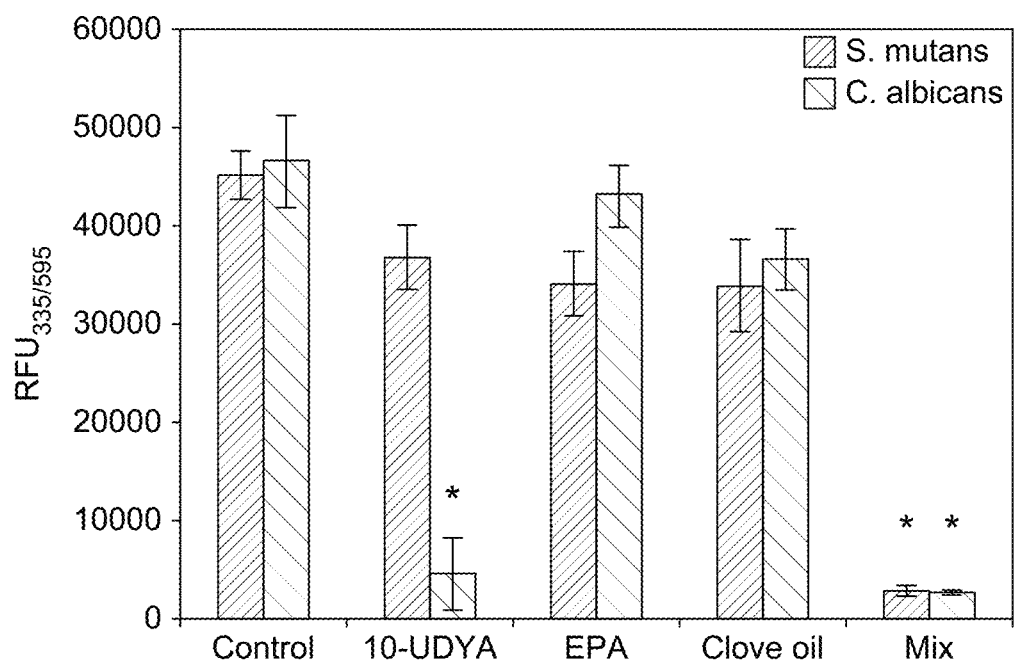
FIG. 9A. 100% mature biofilm biocidal effect was achieved with the test mix at 3550-3025 µg/ml after 24 h incubation with the test mix.

FIG. 9A. 100% mature biofilm biocidal effect was achieved with the test mix at 3550-3025 µg/ml (10-UDYA 2500 µg/ml, EPA 50 µg/ml, clove oil 1000 µg/ml for S. mutans and 10-UDYA 2500 µg/ml, EPA 25 µg/ml, clove oil 500 µg/ml for C. albicans) after 24 h incubation with the test mix.

Figure 9B:
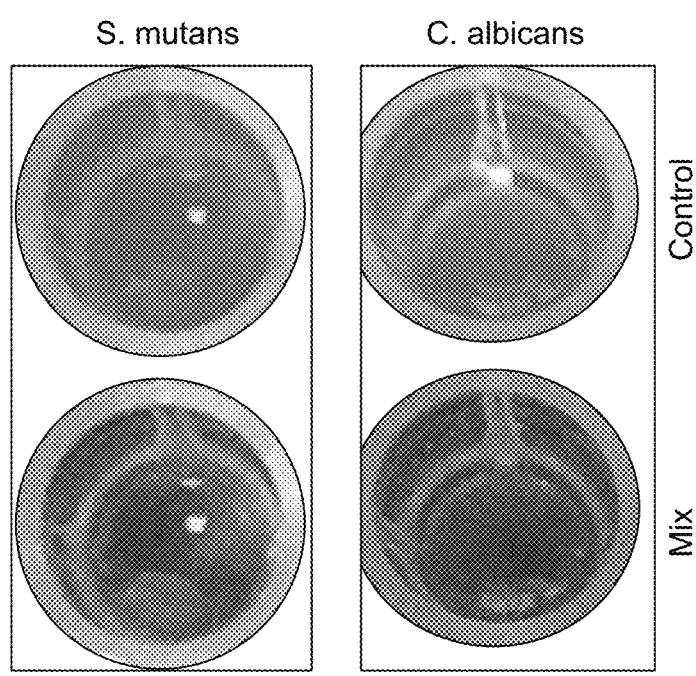
FIG. 9B. Representative images of *Streptococcus mutans* and *Candida albicans* after 24 h incubation period with the test mix at 3550-3025 µg/ml concentration.

FIG. 9B. Representative images of Streptococcus mutans and Candida albicans after 24 h incubation period with the test mix at 3550-3025 µg/ml (10-UDYA 2500 µg/ml, EPA 50 µg/ml, clove oil 1000 µg/ml for S. mutans and 10-UDYA 2500 µg/ml, EPA 25 µg/ml, clove oil 500 µg/ml for C. albicans) after 24 h incubation with the test mix.

Figure 10A:
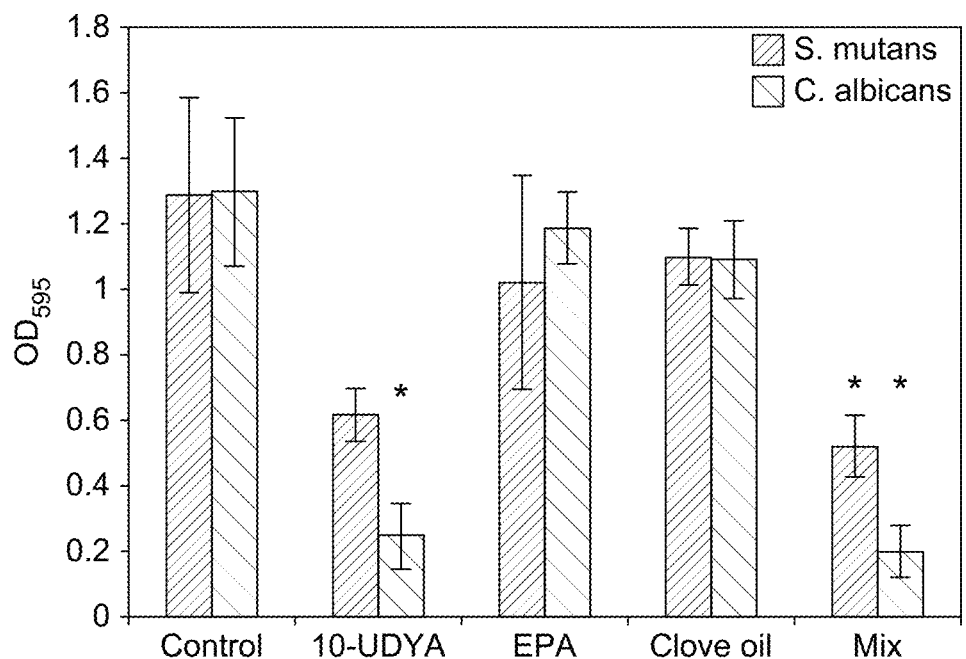
FIG. 10A. 50% *S. mutans* mature biofilm eradication effect was achieved with the test mix at 8050 µg/ml and 100% *C. albicans* mature biofilm eradication effect was achieved with the test mix at 3025 µg/ml after 24 h incubation with the test mix.

FIG. 10A. 50% *S. mutans* mature biofilm eradication effect was achieved with the test mix at 8050 (10-UDYA 7000 μg/ml, EPA 50 μg/ml, clove oil 1000 μg/ml for *S. mutans*) and 100% *C. albicans* mature biofilm eradication effect was achieved with the test mix at 3025 μg/ml (10-UDYA 2500 μg/ml, EPA 25 μg/ml, clove oil 500 μg/ml for *C. albicans*) after 24 h incubation with the test mix.

Figure 10B:
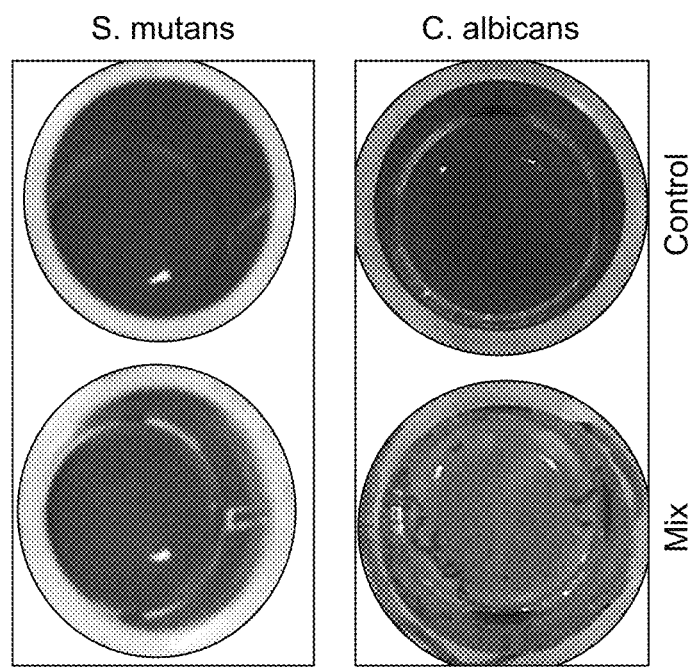
FIG. 10B. Representative images of *Streptococcus mutans* and *Candida albicans* after 24 h incubation period with the test mix at 8050 µg/ml concentration (*S. mutans*) and at 3025 µg/ml concentration (*C. albicans*).

FIG. 10B. Representative images of *Streptococcus mutans* and *Candida albicans* after 24 h incubation period with the test mix at 8050 (10-UDYA 7000 μg/ml, EPA 50 μg/ml, clove oil 1000 μg/ml for *S. mutans*) and 100% *C. albicans* mature biofilm eradication effect was achieved with the test mix at 3025 μg/ml (10-UDYA 2500 μg/ml, EPA 25 μg/ml, clove oil 500 μg/ml for *C. albicans*) after 24 h incubation with the test mix.

What is claimed is:

1. A mixture, consisting of a *B. serrata* Extract, eicosapentaenoic acid, usnic acid, 10-undecynoic acid, clove oil and norspermidine.

2. The mixture of claim 1, wherein at least four different chemical compounds are chosen from the Norspermidine, the Usnic acid, the eicosapentaenoic acid and the *B. serrata* extract.

3. The mixture of claim 2, wherein the Norspermidine is 0.1% of total weight, the Usnic acid is 50 μg/ml, the eicosapentaenoic acid is 50 μg/ml and the *B. serrata* extract is 250 μg/ml.

4. The mixture of claim 1, wherein at least two different chemical compounds are chosen from the Norspermidine at 0.1% of total weight and Usnic acid at 150 μg/ml.

5. The mixture of claim 3: wherein the mixture is used as a dental formulation to kill a *Streptococcus mutans* and yeast *Candida albicans*.

6. The mixture of claim 1, wherein the mixture is in a liquid or paste-like or solid carrier material.

7. The mixture of claim 1, wherein the mixture is used as a treatment in a dental formulation to kill a *Streptococcus mutans* and yeast *Candida albicans* in an oral cavity.

8. The mixture of claim 1, wherein at least three different chemical compounds consist of a 10-undecynoic acid, an eicosapentaenoic acid, and a clove oil.

9. The mixture of claim 8, wherein the concentration of the 10-undecynoic acid is 1000 μg/ml, the eicosapentaenoic acid is 25 μg/ml, and the clove oil is 500 μg/ml.

* * * * *